United States Patent [19]

Luduena

[11] Patent Number: 4,511,501
[45] Date of Patent: Apr. 16, 1985

[54] BIS-AMIDE DISULFIDE CLEAVABLE CROSS-LINKING REAGENTS

[75] Inventor: Richard F. Luduena, San Antonio, Tex.

[73] Assignee: Board of Regents, The University of Texas System, Austin, Tex.

[21] Appl. No.: 551,586

[22] Filed: Nov. 14, 1983

Related U.S. Application Data

[62] Division of Ser. No. 417,026, Sep. 13, 1982.

[51] Int. Cl.$^3$ .................................................. C07G 7/00
[52] U.S. Cl. ................................ 260/112 R; 260/121; 260/117; 260/465.5 R; 564/209
[58] Field of Search .................. 260/112 R, 117, 119, 260/121, 123, 123.5, 123.7

[56] References Cited

U.S. PATENT DOCUMENTS

| | | | |
|---|---|---|---|
| 3,072,707 | 1/1963 | Pierson et al. | 560/18 |
| 3,365,480 | 1/1968 | Cobb, et al. | 260/453 R |
| 3,595,915 | 7/1971 | Emerson et al. | 564/209 |
| 4,101,388 | 7/1978 | Rubinstein et al. | 260/112 R |
| 4,179,514 | 12/1979 | D'Silva | 424/277 |

FOREIGN PATENT DOCUMENTS 2006237  5/1975  United Kingdom .

OTHER PUBLICATIONS

"Evidence of Inactivation of Pineal . . . Exchange", Namboodiri et al., *JBC* 255(13), Jul. 7, 1980, pp. 6032–6035.

*Chem Abstract*, No. 49013y, "Chemical and physico-chemical properties of amino . . . disulfides, vol. 74, 1971, p. 507.

"N,N'-Bis(α-iodoacetyl)-2,2'-dithiobis (ethylamine), . . . Groups", Analytical Chem, 117, (1981), pp. 76-80, Luduena et al.

Double Agents, Bifunctional Cross-Linking Reagents. "N,N-Bis(α-iodoacetyl)-2,2'-dithiobis(ethylamine), a Reversible CrossLinking Reagent for Protein Sulfhydryl Groups", Richard F. Luduena, et al., published Oct. 1981.

Reiner et al., *J. Molecular Catalysis*, 1:3–12, (1975).

*Primary Examiner*—John Kight
*Assistant Examiner*—Garnette D. Draper
*Attorney, Agent, or Firm*—Arnold, White & Durkee

[57] ABSTRACT

Cleavable cross-linking reagents having the general formula:

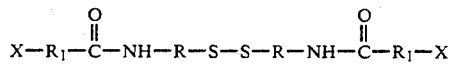

wherein R and R$_1$ are lower alkyl or lower alkenyl groups having one to four carbon atoms and X is a halide. A preferred example of the invention is represented by the formula:

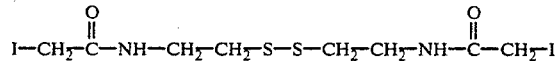

Compounds of the present invention are useful in establishing cleavable cross links between sulfhydryl groups of protein molecules.

6 Claims, No Drawings

BIS-AMIDE DISULFIDE CLEAVABLE CROSS-LINKING REAGENTS

BACKGROUND OF THE INVENTION

The Government has rights in this invention pursuant to National Institutes of Health Grant MH34757.

This is a division of application Ser. No. 417,026, filed 9/13/82.

The present invention relates to disulfide, bis-amide compounds; and more particularly to disulfide, bis-amide compounds reactive with sulfhydryl functional groups. Further, the present invention relates to the use of disulfide bis-amide compounds as cleavable cross-linking reagents specific for nucleophilic groups present on substrate molecules.

Bifunctional cross-linking reagents have proven to be highly useful probes in investigating the tertiary and quaternary structures of proteins and in elucidating the topographies of supramolecular assemblies. Among cross-linking agents, those which generate cross-links cleavable under mild conditions are particularly desirable in studying complex protein assemblies, since cleavage of the cross-link permits easy identification of the cross-linked proteins. The utility of any cross-linking reagent, however, cleavable or not, is limited both by the nature of the functional group on the substrate protein with which the cross-linking agent reacts, and by the length of the cross-link generated by this reaction.

Relatively few readily cleavable cross-linking reagents have been reported. Of these, the majority, such as dimethyl-3,3'-dithiobispropionimidate, dithiobis(succinimidyl propionate) and the tartryl diazides, react largely with amino groups. Other reagents, such as the heterobifunctional 2-iminothiolane, are able to generate a cleavable cross-link between an amino and a sulfhydryl group.

With one class of exceptions, none of the reversible cross-linking reagents yet described, however, can make covalent cross-links between two sulfhydryl groups. The only exceptions are reagents such as di-1,10-phenanthroline-Cu(II) cation which can oxidize two adjacent sulfhydryl groups or sulfhydryl groups very close together in the tertiary structure to generate a disulfide bridge. The required close proximity of the sulfhydryl groups, however, limits the general usefulness of this type of reagent.

When using cross-linking techniques to investigate a complex protein structure, it would be helpful to have a battery of reversible cross-linking reagents differing in their functional group specificities and chain lengths.

So far as applicant is aware, no reagents have been reported to date which are able to generate cleavable crosslinks between two cysteine residues that are not close neighbors in the tertiary structure.

Accordingly, there remains a need for a reagent which can generate cleavable cross-links between non-adjacent sulfhydryl groups. Such compounds and methods are provided by this invention.

SUMMARY OF THE INVENTION

In accordance with this invention, there are provided disulfide compounds represented by the formula:

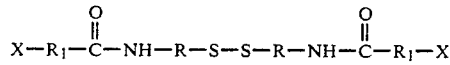

wherein R and $R_1$ are lower alkyl or lower alkenyl groups having one to four carbon atoms and X is a functional group capable of participating in a nucleophilic substitution reaction. X can function as either a leaving group or displacing nucleophile in a nucleophilic substitution reaction.

The compounds of the present invention are useful as cleavable cross-linking reagents between nucleophilic functional groups present on a substrate molecule. Cross-linking can be established either intramolecularly or intermolecularly.

DETAILED DESCRIPTION OF PREFERRED EMBODIMENTS

The invention will be described in terms of preferred embodiments which represent the best mode known to the applicants at the time of this application.

In accordance with such preferred embodiments, applicant provides a reversible, bifunctional cross-linking agent reactive with nucleophilic functional groups of a substrate molecule and particularly reactive with non-adjacent sulfhydryl groups. Particularly, preferred by applicant is a symmetrical bifunctional disulfide analogue of iodoacetamide, termed N,N'-bis(α-iodoacetyl)-2,2'-dithiobis(ethylamine)(BIDBE) and represented by the structure:

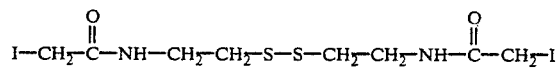

This compound reacts with protein sulfhydryl groups under mild conditions and forms easily cleavable cross-links between polypeptide chains. From the given structure of BIDBE, it can cross-link between sulfhydryl groups up to 18 Å apart.

Extensions of the R and $R_1$ groups provide variability in the binding capacity to more distant sulfhydryl groups. It is preferred however to extend the R group rather than $R_1$ so as to preserve the electron withdrawing capacity of the amide function.

Further, the reactive functional group X is preferrably iodide, I—, but desirably other halides such as bromide, chloride, or fluoride can be substituted.

It should be noted that the reaction between the compounds of the present invention and the cross-linked sulfhydryl are a form of nucleophilic substitution. Accordingly in the preferred embodiment, X is the leaving group and the sulfhydryl group is the displacing nucleophile. Having this in mind, the order of reactivity of the leaving group X typically increases with basicity of the displacing group.

Generally, as contemplated in the practice of this invention with respect to cross-linking proteins, there are two major nucleophilic displacing groups present in proteins, the amine function and —SH. The amine nucleophile for almost all proteins predominates, since there are relatively few —SH groups in a protein molecule. When examining the reactive basicity of nucleophiles, in most instances the sulfhydryl group is more nucleophilic than the amine function. However, since the amine function predominates and is generally sterically available, most cross-linking agents react preferrably with amine functions.

To induce specificity with the sulfhydryl group over that of amine functions, it is preferred that the functional group X be a nucleophile less basic than —SH but more basic than amine functions, —NRH or —NH$_2$. Or in other words X is less nucleophilic than —SH, but more nucleophilic than the amine functions. Ideally, iodide is the preferred functional group X in selective cross-links between sulfhydryl groups. Another preferred reactive group X is —CN, but cyanide groups have toxicity problems associated with their subsequent HCN production.

The compounds of this invention are readily prepared by a variety of reactions. For example, reaction of bis-amino disulfides with halogenated acetyl anhydrides or halogenated acetates results in symmetrical disulfide bis-amide compounds.

The specific examples which follow are presented as merely illustrative, non-limiting demonstrations of the preparation of the compounds of the instant invention and their effectiveness in cross-linking non-adjacent sulfhydryl groups present in protein structures.

In the examples which follow the following materials were employed:

Iodoacetic anhydride was purchased from Alfa Products, Danvers, Mass., 1,2-dichloroethane from the Aldrich Chemical Co., Milwaukee, Wis., cystamine diHCl, iodoacetamide and rabbit muscle aldolase from the Sigma Chemical Co., St. Louis, Mo., and dimethylsulfoxide (Me$_2$SO) from the Fisher Scientific Co., Fairlawn, N.J. Iodo(1-$^{14}$C)acetamide was purchased from the Amersham Corporation, Arlington Heights, Ill. It was diluted with cold iodoacetamide and its specific activity determined as previously described in *Biochemistry* 20:4437–4444 (1981). Microtubules were prepared from bovine cerebra by the method of Fellous et al. *Eur. J. Biochem.* 78:167–174 (1977). Tubulin was purified from microtubule protein by chromatography on phosphocellulose (Whatman P11) as described in Fellous et al., supra.

Mass spectra were determined on a Hewlett-Packard model 5982 quadrupole mass spectrometer in combination with a Hewlett-Packard model 5933 data system. The sample was introduced through a direct inlet and was heated to effect volatilization. With a source pressure of $1 \times 10^{-7}$ Torr, a temperature range of 38° to 150° C. was employed. The ion source temperature was 175° C. and the electron energy was 70 eV.

EXAMPLE I

N,N'-bis(α-iodoacetyl)-2-2'-dithiobis(ethylamine)(-BIDBE) was prepared as follows.

1.0 ml of a 0.018M solution of cystamine diHCl in 0.1N NaOH was mixed in a test tube with 0.25 ml of a 0.22M solution of iodoacetic anhydride in 1,2-dichloroethane. The tube was agitated on a vortex mixer for 1 min and the resulting white precipitate was collected by centrifugation at 12,000×g for 15 min at 20° C. The precipitate was then dried in vacuo. In order to remove any iodoacetate that could have formed as a by-product, the precipitate was dissolved in acetone and centrifuged at 12,000×g for 15 min at 15° C. The pellet, which consisted largely of iodoacetate, was discarded and the supernatant, containing BIDBE, was dried under a stream of N$_2$.

In the mass spectrum of BIDBE, no molecular ion at m/z 488 was observed. The peak of highest mass was found at m/z 361 representing M-127 (iodine). Fission between the two sulfur atoms gave a small peak at m/z 244. When an atom of iodine was also lost, an ion at m/z 117 was observed. Loss of a fragment containing both sulfur atoms gave peaks at m/z 212 (with iodine) and m/z 85 (without iodine). The peak at m/z 30, attributed to CH$_2$=N$^+$H$_2$, arises from migration of a hydrogen atom on the iodoacetyl portion of the molecule combined with cleavage of a bond α to the nitrogen. The fragmentation pattern of the mass spectrum is in agreement with the following proposed structure for BIDBE:

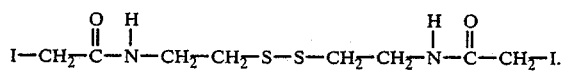

EXAMPLE II

Reaction of BIDBE with aldolase.

To 0.25 ml of a 7.15 mg/ml solution of aldolase in 0.05M Tris-HCl, pH 8.0, was added 10 μl of a 34.1 mM solution of BIDBE, freshly dissolved in Me$_2$SO. The final concentration of BIDBE was 1.31 mM and the molar ratio of BIDBE to aldolase sulfhydryls was 0.95:1. The incubation was carried out for 3.5 hr at 25° C. in the dark. A control sample of aldolase, 3.8% in Me$_2$SO, but not reacted with BIDBE, was incubated under the same conditions. At the end of the incubation, the samples were dialyzed for 16 hr at 1° C. in the dark against 0.059M Tris-phosphate, pH 7.0, containing 20% sucrose. Each sample was then made 1% in Na dodecyl sulfate and divided into two aliquots. One aliquot from each sample was made 1% in β-mercaptoethanol and then all the samples were incubated for 1 min at 100° C. The samples were then subjected to electrophoresis on 8% polyacrylamine gels containing 0.1% Na dodecyl sulfate according to methods set out in Laemmli, *Nature* (London) 227:680–685 (1970). The gels were stained with fast green and scanned at 640 nm using a Gilford 250 spectrophotometer equipped with a linear transport. The areas of the peaks were determined by planimetry.

Treatment of aldolase with BIDBE produced a cross-linked dimer of aldolase as shown by polyacrylamine gel electrophoresis. The fact that these products were stable to incubation at 100° C. in the presence of 1% Na dodecyl sulfate suggests that they are held together by covalent linkages. Altogether, 52% of the aldolase was cross-linked as determined by quantitative gel scanning. 50% of this cross-linked material behaved as a cross-linked dimer of two aldolase subunits. When BIDBE-treated aldolase was incubated with β-mercaptoethanol (a cleaving agent) prior to gel electrophoresis, the cross-linked dimer was no longer present and only the monomer was seen. Thus, it appears that BIDBE can produce cleavable covalent cross-links between aldolase subunits. In this study, no attempt was made to determine whether the polypeptides cross-linked by BIDBE were in the same or in different aldolase tetramers.

EXAMPLE III

Reaction of BIDBE with tublin.

To each of three 0.255 ml aliquots of a 0.74 mg/ml solution of tubulin in 100 mM Mes$^a$, 1 mM EGTA$^b$, 0.1 mM EDTA$^c$, 0.5 mM MgCl$_2$, 1 mM GTP$^d$ buffer pH 6.4 were added 5 μl of a 34.1 mM solution of BIDBE in Me₂SO. The final concentration of BIDBE was 0.655 mM. The incubation was carried out for 1 hr at 37° C. in the dark. For comparison, one set of aliquots of tubulin was incubated in the presence of 1.31 mM iodoacetamide instead of BIDBE and a control set was incubated without either BIDBE or iodoacetamide. All samples were 1.9% in Me₂SO. At the end of 1 hr, 5 μl of ($^{14}$C)iodoacetamide (0.46 Ci/mole) were added to each sample to give a final concentration of 1.29 mM. The incubation was continued at 37° C. for 1 hr and then the tubulin in each sample was precipitated by treatment with an equal volume of 10% trichloroacetic acid. The precipitates were collected on Celotate filters and the radioactivity of the filters determined as previously described in Luduena et al. *Biochemistry* 20:4444–4450 (1981). The structural similarity between BIDBE and iodoacetamide makes it likely that the two reagents would react with the same types of residues in proteins. Iodoacetamide is known to favor reactions with sulfhydryl groups and Luduena et al., *Biochemistry* 20:4437–4444 (1981) have recently shown that when bovine brain tubulin is incubated with ($^{14}$C)iodoacetamide at pH 6.4–6.75, only the sulfhydryl groups, and no others, react with the alkylating agent. When tubulin that had first been treated with 0.655 mM BIDBE was allowed to react with ($^{14}$C)iodoacetamide BIDBE inhibited the reaction of tubulin with ($^{14}$C)iodoacetamide by 86.3±4.8% suggesting that BIDBE was reacting with sulfhydryl groups. When unlabelled iodoacetamide, at a concentration of 1.31 mM, was used in place of BIDBE, it inhibited the reaction with ($^{14}$C)iodoacetamide by 44.1±4.4%.

[a]Mes=2-(N-morpholino)ethanesulfonic acid
[b]EGTA=ethylene glycol bis(β-aminoethyl ether)N,N-tetraacetic acid
[c]EDTA=ethylenediamine tetraacetic acid
[d]GTP=allanosine-5'-triphosphate Analysis of the BIDBE-treated tubulin by polyacrylamide gel electrophoresis did not reveal any cross-linked dimer, indicating that any intra-molecular crosslink formed by BIDBE would have to be intra-chain.

While the compounds and methods of this invention have been described in terms of preferred embodiments it will be apparent to those of skill in the art that various changes may be made in the compounds and methods disclosed without departing from the scope of the invention, which is defined by the following claims:

What is claimed is:

1. A method of selectively establishing a cleavable cross-link between sulfhydryl groups present on a protein substrate molecule comprising:
reacting the sulfhydryl groups with a disulfide compound represented by the formula:

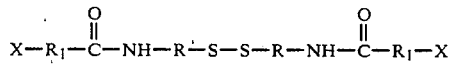

wherein R and R₁ are lower alkyl or lower alkenyl groups having one to four carbon atoms, and X is a halide.

2. The method according to claim 1 wherein the substrate is cross-linked intramolecularly or intermolecularly.

3. The method according to claim 1 wherein X is iodide.

4. The method according to claim 1 wherein R and R₁ are alkyl groups.

5. The method according to claim 1 wherein R is ethylene and R₁ is methylene.

6. The method according to claim 1 having the formula:

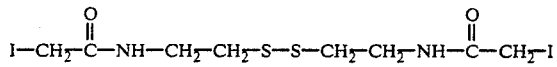

* * * * *